(12) United States Patent
Takulapalli

(10) Patent No.: US 9,170,228 B2
(45) Date of Patent: Oct. 27, 2015

(54) NANO STRUCTURED FIELD EFFECT SENSOR AND METHODS OF FORMING AND USING SAME

(76) Inventor: Bharath R. Takulapalli, Chandler, AZ (US)

( * ) Notice: Subject to any disclaimer, the term of this patent is extended or adjusted under 35 U.S.C. 154(b) by 1475 days.

(21) Appl. No.: 12/663,666

(22) PCT Filed: Jun. 6, 2008

(86) PCT No.: PCT/US2008/066190
§ 371 (c)(1),
(2), (4) Date: Nov. 23, 2011

(87) PCT Pub. No.: WO2009/017882
PCT Pub. Date: Feb. 5, 2009

(65) Prior Publication Data
US 2012/0055236 A1 Mar. 8, 2012

Related U.S. Application Data

(60) Provisional application No. 60/942,952, filed on Jun. 8, 2007.

(51) Int. Cl.
*G01N 27/414* (2006.01)

(52) U.S. Cl.
CPC ......... *G01N 27/4145* (2013.01); *Y10S 977/762* (2013.01); *Y10S 977/936* (2013.01); *Y10S 977/938* (2013.01); *Y10S 977/953* (2013.01); *Y10S 977/957* (2013.01); *Y10S 977/958* (2013.01)

(58) Field of Classification Search
CPC ............ G01N 27/4145; Y10S 977/762; Y10S 977/936; Y10S 977/938; Y10S 977/953; Y10S 977/957; Y10S 977/958

USPC ............ 977/957, 958, 959; 438/49; 257/253, 257/E29.242
See application file for complete search history.

(56) References Cited

U.S. PATENT DOCUMENTS 5,264,395 A * 11/1993 Bindal et al. ............... 438/404
5,334,281 A * 8/1994 Doerre et al. ............... 438/404
5,431,883 A 7/1995 Barraud
(Continued)

FOREIGN PATENT DOCUMENTS

GB 2 389 424 B 11/2004
GB 2 416 210 A 1/2006
(Continued)

OTHER PUBLICATIONS

Takulapalli, B. R., T. J. Thornton, D. Gust, B. Ashcroft, S. M. Lindsay, H. Q. Zhang, and N. J. Tao. "The pH response of a silicon-on-insulator MOSFET with an integrated nanofluidic cell." In SOI Conference, 2003. IEEE International, pp. 114-116.*
(Continued)

*Primary Examiner* — Lisa Caputo
*Assistant Examiner* — Punam Roy
(74) *Attorney, Agent, or Firm* — Snell & Wilmer L.L.P.

(57) ABSTRACT

A solid-state field-effect transistor sensor for detecting chemical and biological species and for detecting changes in radiation is disclosed. The device includes a porous or structured channel section to improve device sensitivity. The device is operated in a fully depleted mode such that a sensed biological, chemical or radiation change causes an exponential change in channel conductance.

25 Claims, 15 Drawing Sheets

(56) References Cited

U.S. PATENT DOCUMENTS

| | | | | |
|---|---|---|---|---|
| 5,683,569 | A | * | 11/1997 | Chung et al. ................ 205/775 |
| 6,111,280 | A | * | 8/2000 | Gardner et al. ............... 257/253 |
| 6,355,532 | B1 | * | 3/2002 | Seliskar et al. ............... 438/283 |
| 6,433,356 | B1 | | 8/2002 | Cahen et al. |
| 6,437,404 | B1 | * | 8/2002 | Xiang et al. ................... 257/347 |
| 6,753,200 | B2 | * | 6/2004 | Craighead et al. ............. 438/48 |
| 7,091,069 | B2 | * | 8/2006 | Doris et al. ................... 438/149 |
| 7,235,440 | B2 | * | 6/2007 | O'Meara et al. ............. 438/240 |
| 7,247,887 | B2 | * | 7/2007 | King et al. .................... 257/139 |
| 7,622,934 | B2 | * | 11/2009 | Hibbs et al. .................. 324/686 |
| 7,947,485 | B2 | * | 5/2011 | Wu et al. .................... 435/283.1 |
| 8,154,093 | B2 | * | 4/2012 | Bradley et al. ............... 257/414 |
| 8,426,900 | B2 | * | 4/2013 | Ahn et al. .................... 257/253 |
| 2002/0117659 | A1 | * | 8/2002 | Lieber et al. ................... 257/14 |
| 2003/0231531 | A1 | | 12/2003 | Baxter et al. |
| 2004/0079636 | A1 | | 4/2004 | Hsia et al. |
| 2004/0132070 | A1 | * | 7/2004 | Star et al. .......................... 435/6 |
| 2004/0144985 | A1 | * | 7/2004 | Zhang et al. .................... 257/79 |
| 2004/0195563 | A1 | * | 10/2004 | Bao et al. ........................ 257/40 |
| 2004/0238379 | A1 | | 12/2004 | Lindsay et al. |
| 2005/0026453 | A1 | * | 2/2005 | O'Meara et al. ............. 438/778 |
| 2005/0056892 | A1 | * | 3/2005 | Seliskar ......................... 257/348 |
| 2006/0113603 | A1 | * | 6/2006 | Currie ........................... 257/368 |
| 2006/0243969 | A1 | | 11/2006 | Bao et al. |
| 2006/0263255 | A1 | * | 11/2006 | Han et al. ........................ 422/83 |
| 2006/0267051 | A1 | | 11/2006 | Gstrein et al. |
| 2007/0063304 | A1 | * | 3/2007 | Matsumoto et al. .......... 257/462 |
| 2008/0283875 | A1 | | 11/2008 | Mukasa et al. |
| 2009/0014757 | A1 | * | 1/2009 | Takulapalli et al. .......... 257/253 |
| 2010/0297608 | A1 | * | 11/2010 | Stern et al. ........................ 435/5 |
| 2011/0088466 | A1 | * | 4/2011 | Frerichs .................... 73/335.02 |
| 2012/0045844 | A1 | * | 2/2012 | Rothberg et al. ............. 436/144 |
| 2012/0286330 | A1 | * | 11/2012 | Kellam .......................... 257/190 |

FOREIGN PATENT DOCUMENTS

| | | | | |
|---|---|---|---|---|
| JP | 2004-309483 | A | | 11/2004 |
| JP | 2005-061960 | A | | 3/2005 |
| WO | WO 2005015193 | A1 | * | 2/2005 ........... G01N 27/414 |
| WO | 2006134942 | A1 | | 12/2006 |
| WO | WO 2014/143954 | | * | 9/2014 |

OTHER PUBLICATIONS

Takulapalli, Bharath Reddy. "Molecular sensing using monolayer gate fully depleted silicon on insulator nano MOSFETs". ProQuest Dissertations and Theses; Thesis (Ph.D.)—Arizona State University, 2006.*

International Preliminary Report on Patentability mailed Dec. 11, 2009 in International Application No. PCT/US2008/066190.

Official Action mailed Jun. 6, 2013 in Japanese Application No. 2010-511384.

Yang, Jinman et al., Molecular Control of the Drain Current in a Buried Channel MOSFET Nanotech 2002 vol. 2.

Bouvet, Marcel, Phthalocyanine-based field-effect transistors as gas sensors, Anal. Bioanal. Chem. (2006) 384: 366-373.

Yang, Jinman et al., Molecular control of the threshold voltage of an NMOS inversion layer, Microelectronic Engineering 63 (2002) 135-139.

Laws, G. M., Drain current control in a hybrid molecular/MOSFET device, Physica E 17 (2003) 659-663.

Yang, Jinman et al., Controlling the threshold voltage of a metal-oxide-semiconductor field effect transistor by molecular protonation of the Si:SiO2 interface, J. Vac. Sci. Technol. B 20(4), Jul./Aug. 2002.

Takulapalli, Bharath, Molecular Sensing Using Monolayer Gate Fully Depleted Silicon on Insulator Nano MOSFETS, Aug. 2006.

International Search Report from PCT/US2008/066190 mailed May 3, 2009.

Written Opinion of the International Searching Authority from PCT/US2008/066190 mailed May 3, 2009.

Shepherd L. et al., Weak Inversion ISFETs for ultra-low power biochemical sensing and real-time analysis, Sensors and Actuators B, Elsevier Sequoia S.A., Lausanne, CH, vol. 107, No. 1, May 27, 2005, pp. 468-473. ISSN: 0925-4005.

Martinoia S. et al., A behavioral macromodel of the ISFET in SPICE, Sensors and Actuators B, Elsevier Sequoia S. A., Lausanne, CH, vol. 62, No. 3, Mar. 1, 2000, pp. 182-189. ISSN: 0925-4005.

Takulapalli Bharath, Detection of Pyridine using ZnTCPP SAM Coated SOI Mosfet Devices, Jun. 9, 2006.

Ashcroft, B., et al. Calibration of a PH Sensitive Buried Channel Silicon-on-Insulator MOSFET for Sensor Applications.

Ouisse et al., "Influence of Series Resistances and Interface Coupling on the Transconductance of Fully-Depleted Silicon-on-Insulator MOSFETS," Solid-State Electronics, vol. 35, No. 2, pp. 141-149, 1992.

Official Action mailed Jan. 15, 2014 in Japanese Application No. 2010-511364.

* cited by examiner

NANO STRUCTURED FIELD EFFECT SENSOR AND METHODS OF FORMING AND USING SAME

CROSS-REFERENCE TO RELATED APPLICATIONS

This application is a U.S. National Phase filing under 35 U.S.C. 371 and claims priority to PCT Application No. PCT/US08/66190, filed on Jun. 6, 2008, and entitled "NANO STRUCTURED FIELD EFFECT SENSOR AND METHODS OF FORMING AND USING SAME," which claims priority to U.S. Provisional Patent Application Ser. No. 60/942,952, filed Jun. 8, 2007, both of which are incorporated herein by reference in their entirety.

FIELD OF INVENTION

The invention generally relates to solid-state sensors. More particularly, the invention relates to field effect sensors, having structured or porous active regions, and to methods of making and using the sensors.

BACKGROUND OF THE INVENTION

Solid-state sensors may be used in a wide variety of applications. For example, chemical solid-state sensors may be used for real-time analysis of chemical mixtures in both continuous and discrete sampling modes. Similarly, biological sensors can be used to detect biological agents and hazards and radiation sensors can be used to detect types and amounts of radiation.

The sensors may be used to detect a single component in a complex mixture, such as a toxic molecule in ambient atmosphere, analyze multiple components in a composition, or perform characterization and quality assessment of complex mixtures—e.g., as used to characterize odors, tastes, smells, etc., by pattern recognition methods using array-based sensors.

Typical solid-state sensors generally include a detection or receptor element and signal transduction means. The receptor layer interacts with the target specie(s)—e.g., by physical absorption or physisorption, chemisorption, microencapsulation, or the like. The transducer converts a change at the receptor surface into a measurable electrical signal. The signal transduction, or coupling of signal between the receptor and the transducer may be linear, nonlinear, logarithmic or exponential in relation. The coupling relation between the two elements generally determines the sensitivity of the device.

A variety of signal transducer elements, such as potentiometric sensors, amperometric sensors, conductometric sensors, field effect transistor (FET) based sensors, optical sensors, thermal sensors, gravimetric or piezo-electric sensors, and the like, have been developed. FET devices may be particularly desirable because the FET devices exhibit relatively fast and sensitive signal transduction, are relatively easy to use, and are relatively easy to integrate with other sensor components.

In the case of FET devices, the metal gate of the field effect transistor device is either replaced or coated with a sensitive thin film, insulator or membrane, which acts as the signal detection element. The FET devices work on the general principal of detecting shifts in localized electric potential due to interactions at the device surface. The FET device transduces a detection event into an electrical signal by way of change in the conductance of the channel region leading to a change in the drain current. The FET device may be operated as a sensor either by biasing the device with constant gate voltage and measuring the change in the current or by detecting the change in gate voltage required to maintain a constant current.

Metal-oxide-semiconductor FET (MOSFET) type sensors are often operated in inversion mode, where inversion current is established in the semiconductor channel by biasing the metal gate of the MOSFET. In these devices, target molecule binding at the sensitive thin film or a change in radiation level modulates the minority charge carrier density in the inversion channel. Hence, inversion current in a bulk p-type MOSFET decreases upon addition of negative charge to the device surface.

Although such devices and transducer elements have been shown to work for some sensing applications, the non-FET devices are relatively bulky and expensive, and the FET-based devices may be relatively unstable and exhibit relatively low sensitivity. Accordingly, improved sensors and methods of making and using sensors are desired.

SUMMARY OF THE INVENTION

The present invention provides a highly sensitive sensor suitable for detecting chemical, biological, and/or radioactive species. While the ways in which the present invention addresses the various drawbacks of the prior art are discussed in greater detail below, in general, the invention provides a field-effect transistor (FET) having a structured or porous channel to improve device sensitivity.

In accordance with various embodiments of the invention, a sensor includes a substrate, an insulator formed overlying the substrate, and a porous or structured channel formed overlying the insulator. In accordance with various aspects of these embodiments, a top surface of the channel layer acts as a receptor or sensitive layer that interacts with chemical, biological, or radioactive species. In accordance with alternative aspects, the sensor further includes a sensitive layer overlying the channel layer.

In accordance with additional embodiments of the invention, the sensor further includes a dielectric layer overlying the channel region. In accordance with some aspects of the exemplary embodiments, the dielectric layer acts as a receptor or sensitive layer that interacts with chemical, biological, or radioactive species.

In accordance with yet further embodiments, the sensor includes a sensitive layer formed overlying the dielectric layer.

In accordance with various additional aspects, a channel thickness ranges from about 3 Angstrom to about 1000 nm.

In accordance with further various aspects, the sensor is configured to operate in a fully depleted mode, such that a negative charge added to the channel, sensitive layer, or the dielectric layer causes an increase in electron inversion channel conductance for n-channel FET devices and addition of positive charge to the n-channel FET decreases the inversion channel conductance, while an addition of a negative charge to the channel, sensitive layer or the dielectric layer of a p-channel device causes a decrease in electron inversion channel conductance and addition of positive charge to the surface increases the inversion channel conductance.

In accordance with yet further embodiments, the sensor includes an additional layer between the channel and the dielectric layer.

In accordance with further embodiments, a sensor includes additional material to form a heterostructure with the channel layer. The additional material may be in the form of one or more layers or discrete islands of one or more layers of material.

In accordance with various additional embodiments of the invention, the sensor is a biological sensor.

In accordance with yet additional embodiments, the sensor is a chemical sensor.

In accordance with yet further embodiments, the sensor is a radiation sensor.

In accordance with additional embodiments of the invention, a method of forming a sensor includes providing a substrate (e.g., a p-type SOI silicon wafer), thinning a channel region layer (e.g., using a wet oxidation followed by a seed layer of dry oxide), forming a doping mask over a portion of the SOI wafer (e.g., by etching a portion of the oxide layer formed using the wet oxidation followed by a seed layer of dry oxide step), forming a doped region within the channel region, forming a mask for source and drain regions, forming the source and drain regions, removing any excess masking materials, optionally, forming device isolation regions (e.g., using photoresist patterning and plasma etching), forming a porous or structured channel region, and forming contacts in the substrate.

In accordance with various aspects of these embodiments, channel pores or structures are formed by patterning the channel region (e.g., using electron beam lithography) and etching (e.g., using SF6 in an REI apparatus) the region to form the pores or structures. In accordance with further aspects of these embodiments, a chemical, biological, and/or radiation sensitive material is formed overlying the channel region. In accordance with yet further aspects, a dielectric layer is formed overlying channel region. In accordance with yet further aspects, a sensitive layer is formed overlying the dielectric layer. And, in accordance with yet additional aspects of the invention, one or more additional material layers may be included in the sensor structure.

In accordance with alternative embodiments of the invention, a local oxidation of silicon (LOCOS) process is used to achieve device isolation. In accordance with various aspects of these embodiments, the method includes providing an SOI wafer, selectively etching silicon in the channel region of the device to a predetermined depth (e.g., using a reactive ion etch), forming pores or structures in the channel region, forming a diffusion mask layer, forming a field oxide (e.g., using a wet oxidation process) to consume silicon in the channel region, doping a portion of the device, and forming substrate contacts. In accordance with further aspects of these embodiments, a chemical, biological, and or radiation sensitive material is formed overlying the channel region. In accordance with yet further aspects, a dielectric layer is formed overlying the channel region. In accordance with yet further aspects, a sensitive layer is formed overlying the dielectric layer. And, in accordance with yet additional aspects of the invention, one or more additional material layers may be included in the sensor structure.

In accordance with yet further embodiments, the sensor is formed using flexible sensor technology.

In accordance with yet further embodiments of the invention, a chemical, biological, or radioactive species is sensed using a fully-depleted exponentially-coupled FET, having a structured or porous channel region.

Elements in the figures are illustrated for simplicity and clarity and have not necessarily been drawn to scale. The dimensions of some of the elements in the figures may be exaggerated relative to other elements to help to improve understanding of embodiments of the present invention.

DETAILED DESCRIPTION

The present invention provides an improved solid-state sensor for detection of biological and chemical species and for radiation detection. More particularly, the invention provides a field-effect transistor (FET) including a porous or structured channel region, which operates as a fully-depleted, exponentially-coupled (FDEC) sensor. As discussed in greater detail below, a threshold voltage or channel conductance of the sensor is manipulated as sensed biological, chemical, or radioactive species are detected, causing an exponential change in channel current.

The exponential change of channel current of the sensors of the present invention is in an opposite direction compared to that of typical FET sensors, and increases in n-channel type devices upon detection of species having excess electron charge or negative charge. Such an exponential response makes the sensors of the present invention more sensitive for qualitative and quantitative analysis.

Figure 1:
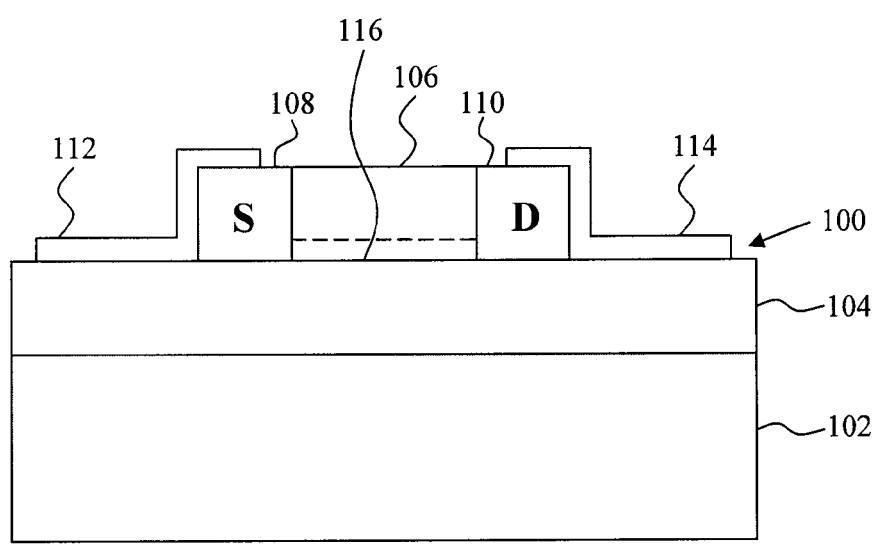
FIG. 1 illustrates a sensor in accordance with various embodiments of the present invention.

FIG. 1 illustrates a sensor 100 in accordance with various embodiments of the invention. Sensor 100 includes a base or substrate 102, an insulator layer 104, a channel region 106, a source 108, a drain 110, and contacts 112, 114. As discussed in more detail below, in accordance with various aspects of exemplary embodiments of the invention, channel region 106 is porous and/or structured.

In operation, sensor 100 is operated in inversion mode, where an inversion current is established in channel region 106 by biasing gate or base 102. As target molecules bind to a surface of sensor 100, the inversion threshold voltage is thought to be modulated by a second-order capacitive charge coupling mechanism involving interface defect states, resulting in an exponential increase in device response. This unique exponential coupling of the device response to the surface charge imparted by the target species on the sensor surface leads to the fully-depleted exponentially-coupled (FDEC) sensor.

In contrast to the present invention, the prior art teaches inversion-based FET devices applied for chemical sensing, with variations of device structure in a manner where addition of negative charge to the surface of an n-channel FET causes a decrease in inversion channel conductance (or drain current decrease), and addition of positive charge causes an increase in inversion channel conductance; and where, in a p-channel FET, addition of negative charge to the surface of the device causes an increase in channel conductance (or drain current increase) and addition of positive charge causes a decrease in channel conductance. Such response of device structures is in opposite direction to the device of the present invention. As noted above, in accordance with various embodiments of the invention, the addition of negative charge to the surface of an n-channel inversion based FET device in accordance with the present invention increases the inversion channel conductance, and addition of positive charge to the surface decreases the inversion channel conductance, while addition of negative charge to the surface of a p-channel inversion based device decreases the inversion channel conductance and addition of positive charge to the surface increases the inversion channel conductance.

Referring again to FIG. 1, base 102 acts as a gate during sensor 100 operation. Base 102 may be formed of any suitable material. Examples include, but are not limited to metals and metal nitrides such as Ge, Mg, Al, Sc, Ti, V, Cr, Mn, Fe, Co, Ni, Cu, Zn, Ga, Y, Zr, Nb, Mo, Ru, Rh, Pd, Ag, La, Hf, Ta, W, Re, Os, Ir, Pt, Au, TaTi, Ru, HfN, TiN, and the like, metal alloys, semiconductors, such as Group IV (e.g., silicon) Group III-IV (e.g., gallium arsenide) and Group II-VI (e.g., cadmium selenide), metal-semiconductor alloys, semi metals, or any organic or inorganic material that acts as a MOSFET gate.

A thickness of base 102 may vary according to material and application. In accordance with one example, base 102 is substrate silicon in silicon-on-insulator (SOI) wafer. In another example, base 102 is a flexible substrate, for example, an organic material, such as Pentacene.

Insulator layer 104 acts as a gate insulator or gate dielectric during operation of sensor 100. Layer 104 may be formed of any suitable material, such as any suitable organic or inorganic insulating material. Examples include, but are not limited to, silicon dioxide, silicon nitride, hafnium oxide, alumina, magnesium oxide, zirconium oxide, zirconium silicate, calcium oxide, tantalum oxide, lanthanum oxide, titanium oxide, yttrium oxide, titanium nitride, and the like. One exemplary material suitable for layer 104 is a buried oxide layer in an SOI wafer. A thickness of layer 104 may vary according to material and application. By way of one particular example, layer 104 is silicon oxide having a thickness from about 1 nm to 100 microns; in accordance with other aspects, layer 104 may be 1 mm or more.

Channel region 106 may be formed of a variety of materials, such as crystalline or amorphous inorganic semiconductor material, such as those used in typical MOS technologies. Examples include, but are not limited to, elemental semiconductors, such as silicon, germanium, diamond, tin; compound semiconductors, such as silicon carbide, silicon germanium, diamond, graphite; binary materials, such as aluminum antimonide (AlSb), aluminum arsenide (AlAs), aluminum nitride (AlN), aluminum phosphide (AlP), boron nitride (BN), boron phosphide (BP), boron arsenide (BAs), gallium antimonide (GaSb), gallium arsenide (GaAs), gallium nitride (GaN), gallium phosphide (GaP), indium antimonide (InSb), indium arsenide (InAs), indium nitride (InN), indium phosphide (InP), cadmium selenide (CdSe), cadmium sulfide (CdS), cadmium telluride (CdTe), zinc oxide (ZnO), zinc selenide (ZnSe), zinc sulfide (ZnS), zinc telluride (ZnTe), cuprous chloride (CuCl), lead selenide (PbSe), lead sulfide (PbS), lead telluride (PbTe), tin sulfide (SnS), tin telluride (SnTe), bismuth telluride ($Bi_2Te_3$), cadmium phosphide ($Cd_3P_2$), cadmium arsenide ($Cd_3As_2$), cadmium antimonide ($Cd_3Sb_2$), zinc phosphide ($Zn_3P_2$), zinc arsenide ($Zn_3As_2$), zinc antimonide ($Zn_3Sb_2$), other binary materials such as lead(II)iodide ($PbI_2$), molybdenum disulfide ($MoS_2$), gallium selenide (GaSe), tin sulfide (SnS), bismuth sulfide ($Bi_2S_3$), platinum silicide (PtSi), bismuth(III)iodide ($BiI_3$), mercury(II)iodide ($HgI_2$), thallium(I)bromide (TlBr), semiconducting oxides like zinc oxide, titanium dioxide ($TiO_2$), copper(I) oxide ($Cu_2O$), copper(II) oxide (CuO), uranium dioxide ($UO_2$), uranium trioxide ($UO_3$), 6.1 Å materials or ternary materials, such as aluminum gallium arsenide (AlGaAs, AlxGa1-xAs), indium gallium arsenide (InGaAs, InxGa1-xAs), aluminum indium arsenide (AlInAs), aluminum indium antimonide (AlInSb), gallium arsenide nitride (GaAsN), gallium arsenide phosphide (GaAsP), aluminum gallium nitride (AlGaN), aluminum gallium phosphide (AlGaP), indium gallium nitride (InGaN), indium arsenide antimonide (InAsSb), indium gallium antimonide (InGaSb), cadmium zinc telluride (CdZnTe, CZT), mercury cadmium telluride (HgCdTe), mercury zinc telluride (HgZnTe), mercury zinc selenide (HgZnSe), lead tin telluride (PbSnTe), thallium tin telluride ($Tl_2SnTe_5$), thallium germanium telluride ($Tl_2GeTe_5$) and quaternary materials, such as aluminum gallium indium phosphide (AlGaInP, InAlGaP, InGaAlP, AlInGaP), aluminum gallium arsenide phosphide (AlGaAsP), indium gallium arsenide phosphide (InGaAsP), aluminum indium arsenide phosphide (AlInAsP), aluminum gallium arsenide nitride (AlGaAsN), indium gallium arsenide nitride (InGaAsN), indium aluminum arsenide nitride (InAlAsN), copper indium gallium selenide (CIGS), or quinary materials like gallium indium nitride arsenide antimonide (GaInNAsSb), and the like.

Channel Region 106 can also be made of organic semiconducting materials. Examples of such materials include, but are not limited to, polyacetylene, polypyrrole, polyaniline, Rubrene, phthalocyanine, poly(3-hexylthiophene, poly(3-alkylthiophene), α-ω-hexathiophene, Pentacene, α-ω-dihexyl-hexathiophene, α-ω-dihexyl-hexathiophene, poly(3-hexylthiophene), bis(dithienothiophene, α-ω-dihexyl-quaterthiophene, dihexyl-anthradithiophene, n-decapentafluoroheptylmethylnaphthalene-1,4,5,8-tetra-carboxylic di imide, α-ω-dihexyl-quinquethiophene, N,N'-dioctyl-3,4,9,10-perylene tetracarbozylic, CuPc, methanofullerene, [6,6]-phenyl-C61-butyric acid methyl ester (PCBM), C60, 3',4'-dibutyl-5-5bis(dicyanomethylene)-5,5'-dihydro-2,2':5',2"terthiophene (DCMT), PTCDI-C5, P3HT, Poly(3,3"-dialkyl-terthiophene), C60-fused N-methylpyrrolidine-meta-C12 phenyl (C60MC12), Thieno[2,3-b] thiophene, PVT, QM3T, DFH-nT, DFHCO-4TCO, BBB, FTTTTF, PPy, DPI-CN, NTCDI, F8T2-poly[9,9'dioctylfluorene-co-bithiophene], MDMO-PPV-poly[2-methoxy-5-(3,7-dimethyloetyloxy)]-1,4-phenylenevinylene, P3HT-regioregular poly[3-hexylthiophene]; PTAA, polytriarylamine, PVT-poly-[2,5-thienylene vinylene], DH-5T-α,ω-Dihexylquinquethiophene, DH-6T-α,ω-dihexylsexithiophene, phthalocyanine, α-6T-α-sexithiophene, NDI, naphthalenediimide, F16CuPc-perfluorocopperphthalocyanine, perylene, PTCDA-3,4,9,10-perylene-tetracarboxylic dianhydrid and its derivatives, PDI—N,N'-dimethyl 3,4,9,10-perylene tetra-carboxylicdiimide, or the like.

A thickness of region 106 may vary according to material and application. By way of one particular example, region has a thickness from about 10 Angstroms to about 10 millimeters. A width of channel region 106 can range from about 10 Angstroms to about 10 millimeters.

As noted above, in accordance with various embodiments of the invention, channel region 106 includes pores and/or structures to increase the device sensitivity.

Figure 4A:
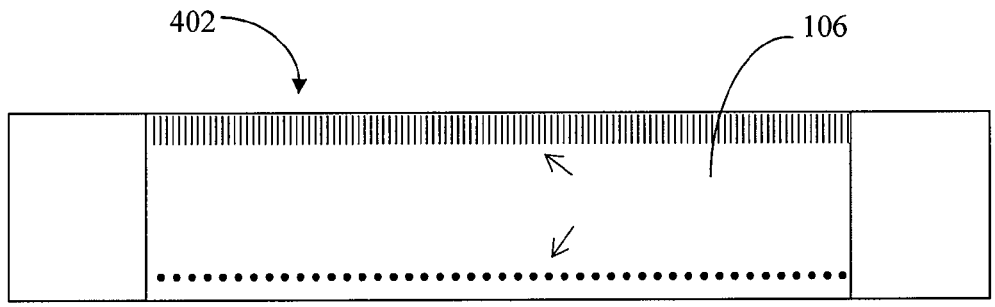
FIGS. 4*a* and 4*b* illustrate channel regions with pores and structures in accordance with various embodiments of the invention.
Figure 4B:
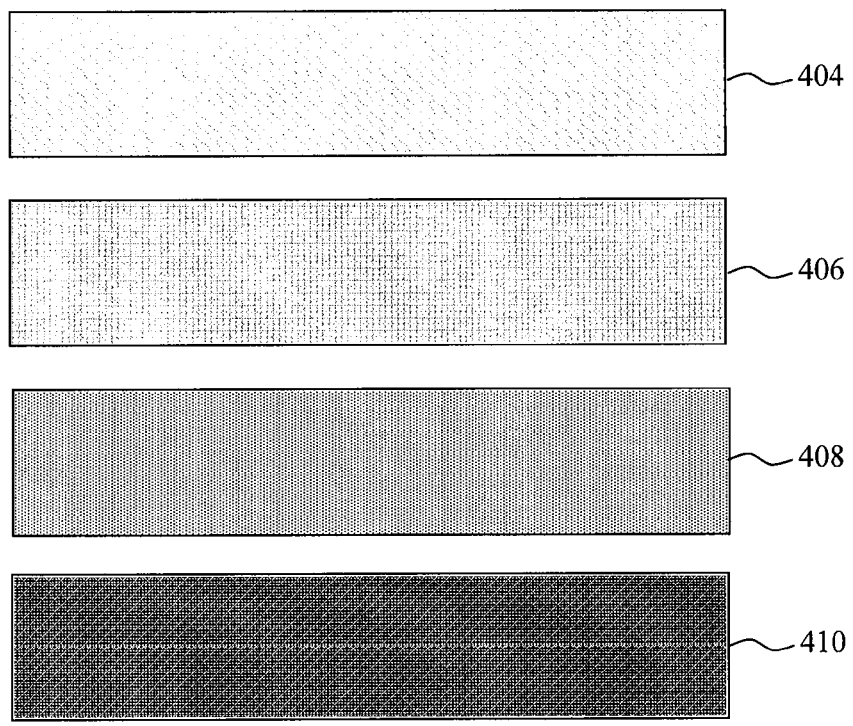

FIGS. 4a and 4b illustrate various examples of such structures and pores. Channel region 106 may include the structures or pores throughout the region thickness, or the structures and/or pores may be formed on a top surface 402 of region 106. In accordance with various examples of the invention, top surface 402 of region 106 includes micro-pores, meso-pores, nano-pores, or macro-pores 404—i.e., the pore diameter size may range from about 3 Å to 100 microns or from about 10 Å to about 10 mm. In accordance with additional embodiments of the invention, a channel region 106 includes structures 406-408, such as nano-structures or micro structures, having dimensions ranging from about 3 Å to about 100 microns. A width of each of the structures can be from about 10 Angstroms to about 10 millimeters. The structures may include, for example, nano or micro scale pillars of square, circular, triangular, hexagonal, any suitable cross section. The structures may also include micro or meso or nano porous structure superimposed on a nano or micro pattern in relief or recess 410.

As discussed in more detail below, the pores and/or structures may be formed using a variety of techniques, such as electron beam lithography, patterning, template based selective etching, electrochemical etching, stain etching, CVD deposition of silicon, molten state imprinting, laser etching, ion etching, particle etching, e-beam etching, chemically enhanced laser ablation, or any other structuring technique to form crisscross patterns, line patterns, pillars, any other patterns, or porous structures or porous structure superimposed on any of these patterns, which act in a way to increase the net surface area of the device surface, where region 106 material remains continuous and crystalline in nature, and hence increase the interaction with interface states.

During operation of sensor 100, an inversion channel 116 is formed at the channel region 106/insulator layer 104 interface by controlling a voltage bias at base 102. Alternatively an inversion channel 116 may be formed in channel region 106 with no bias on base 102, depending of channel region 106 doping, thickness of region 106, and other such variables, and the fixed oxide charge density and interface trap states density at channel 106 boundaries. A thickness of channel region 106 can be from about 1 nm about to about 10 microns, depending on the material and its doping density.

When biasing base 102 to obtain an inversion channel in channel region 106, the thickness (t) of channel region 106 should be such that the whole thickness of channel region 106 should be fully depleted before the formation of inversion channel at channel region 106—insulator 104 interface, as illustrated in the following formula for depletion width at inversion $$\text{thickness}(t) < \text{depletion-width}(w) \sim \sqrt{\frac{4k\varepsilon_o \Phi_F}{qN_{A/B}}}$$

where,
k is the relative dielectric constant of semiconductor
$\varepsilon_o$ is the permittivity of free space
q is the electron charge
$N_{A/B}$ is the concentration of donors/acceptors
$\Phi_F$ is the potential difference between Fermi level and intrinsic level in the semiconductor.

The above equation defines a thickness (t) of channel region 106, in one case, as suitable in device of one example of the present invention, and is less than the full depletion width (w) of the given semiconductor material.

For example, in the case of channel region 106 being a silicon thin film, if the doping density is 1 E 17, a thickness of the channel region 106 should be less than about 200 nm. Whereas, if the doping density is 1 E 14, the thickness of the layer is less than about 4 microns. Stated another way, a thickness of inversion layer 116 is less than the depletion layer width for the given doping density in channel region 106.

Channel region 106 may be doped p-type or n-type, corresponding to n-channel devices and p-channel devices, respectively. The above equation corresponds to a case of a channel region 106 with no extra delta doping profile or similar other extra steps used to modulate the conductance of the channel region, inversion threshold, or the like. In cases of use of delta doping or the like in channel region 106, the analysis and the thickness of channel region 106 will vary accordingly.

One exemplary channel region 106 includes 1 E 15 doped p-type silicon layer of thickness about 100 nm. An inversion layer is formed in this silicon thin film at the silicon—buried oxide interface by biasing base 102.

Source and drain doped regions 108, 110 are formed on either side of the channel region 106 using known doping techniques. In accordance with one example, source and drain regions are 1 E 19 phosphorous doped N++ regions formed in a p-type silicon.

Figure 2:
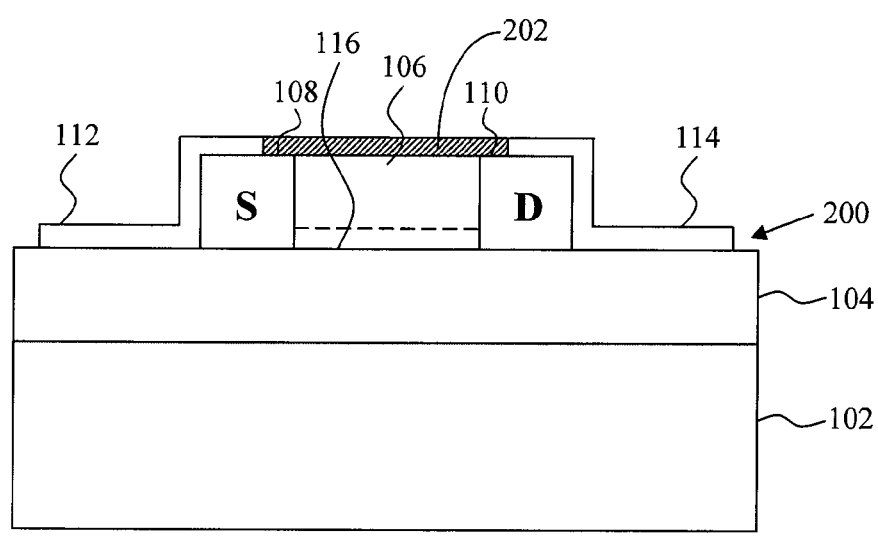
FIG. 2 illustrates a sensor in accordance with additional embodiments of the invention.

FIG. 2 illustrates another sensor 200 in accordance with additional exemplary embodiments of the invention. Sensor 200 is similar to sensor 100, except sensor 200 includes an additional dielectric layer 202. Exemplary materials suitable for dielectric layer 202 include inorganic dielectric material that acts as a gate dielectric material. Examples include, but are not limited to, $SiO_2$, $Si_3N_4$, SiNx, $Al2O_3$, AlOx $La2O_3$, $Y2O_3$, $ZrO_2$, $Ta_2O_5$, $HfO_2$, $HfSiO_4$, HfOx, $TiO_2$, TiOx, a-$LaAlO_3$, $SrTiO_3$, $Ta_2O_5$, $ZrSiO_4$, BaO, CaO, MgO, SrO, $BaTiO_3$, $Sc_2O_3$, $Pr_2O_3$, $Gd_2O_3$, $Lu_2O_3$, TiN, $CeO_2$, BZT, BST, or a stacked or a mixed composition of these and/or such other gate dielectric material(s).

Dielectric layer 202 can additionally or alternatively include an organic gate dielectric material. Examples of organic materials include, but are not limited to, PVP—poly (4-vinyl phenol), PS—polystyrene, PMMA—polymethylmethacrylate, PVA—polyvinyl alcohol, PVC—polyvinylchloride, PVDF—polyvinylidenfluoride, PαMS—poly[α-methylstyrene], CYEPL—cyano-ethylpullulan, BCB—divinyltetramethyldisiloxane-bis(benzocyclobutene), CPVP-Cn, CPS-Cn, PVP-CL, PVP-CP, polynorb, GR, nano $TiO_2$, OTS, Pho-OTS, various self assembled monolayers or multilayers or a stacked or a mixed composition of these and such other organic gate dielectric material.

Dielectric layer 202 can also be of material that is an intrinsic or lowly doped semiconducting material, with low density of charge carriers and low carrier mobility, which is semi-insulating in nature.

In accordance with exemplary aspects of various embodiments of the invention, the processing and fabrication of dielectric layer 202 is done in a controlled fashion, such that the interface state density levels and other such defect states at the layer 202-channel region 106 interface are "optimized." For example, use of Si[111]-SiO2 interface produces larger interface state density compared to Si[100]-SiO2 interface. Optimization of traps does not necessarily mean maximization of interface state density levels, but means application-specific control of interface state densities at that interface in order to manipulate or maximize the resulting sensor signal. In one case, the dielectric layer 202 material is chosen to be a material that acts as both dielectric layer and chemical sensitive layer at the same time. An example of this is use of yttrium oxide ($Y2O_3$) as the gate dielectric, which can be used to sense sulfur mustard gas, since $Y_2O_3$ reacts with mustard gas.

A thickness of layer 202 may vary from application to application and is typically between about 2 Angstroms and 100 nm.

Figure 3:
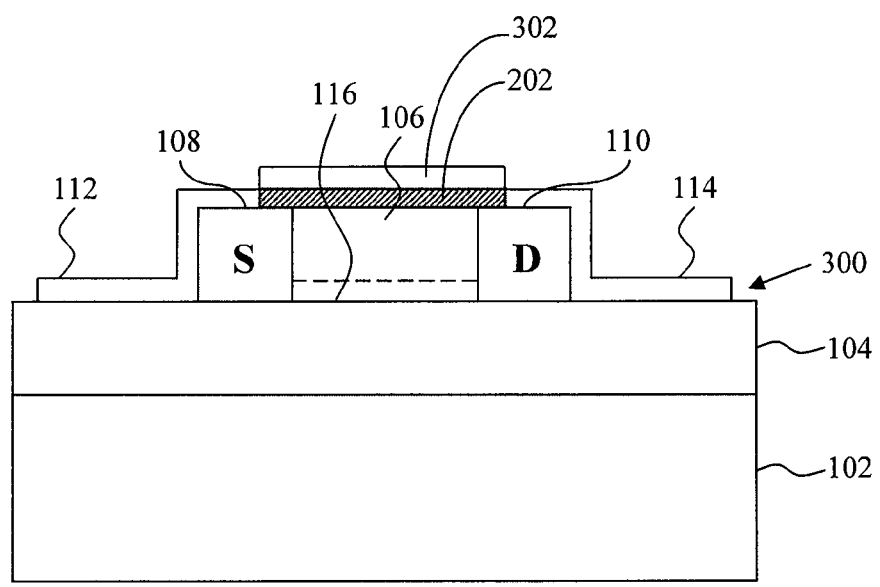
FIG. 3 illustrates a sensor in accordance with yet further embodiments of the invention.

FIG. 3 illustrates another sensor 300 in accordance with additional embodiments of the invention. Sensor 300 is similar to sensor 200, except sensor 300 includes an additional layer 302, which is sensitive to biological, chemical, and/or radioactive material.

Layer 302 is designed to be sensitive to species in the ambient, in, for example, gas phase or in liquid phase. Layer 302 could also be chosen to be sensitive to radiation, where it is applied as a radiation sensitive device.

Layer 302 can be organic or inorganic or conducting or insulating or semiconducting or metallic in nature and can include any suitable material. A thickness of layer 302 can be generally from about 1 Angstrom to about 1000 nanometers. One exemplary material for layer 302 is a zinc porphyrin molecular monolayer that can be used to detect an amine molecule, piperidine.

Layer 302 can be in the form of a continuous layer, particles of various sizes, discrete islands of material, a semi-continuous layer, a stack of layers of different materials, combinations of these structures, or the like, which acts to interact selectively with various biological, chemical, and/or radioactive species. In accordance with additional embodiments of the invention, further layers, that may be continuous, semi-continuous, discrete islands, or particles, can be added above layer 302 in order to increase the capacitive coupling of charge with the interface trap density at the channel region 106-dielectric layer 202 interface, and, in turn, inversion layer 116 formed in channel region 106.

Particular exemplary materials suitable for layer 302 include:

Antibody: antigen binding specific organic or inorganic molecules or biomolecules can be detected with high sensitivity and selectivity using a device coated with antibody(s) or antigen(s) biomolecules. For example, a sensor including a biotin layer can be used to detect Avidin and Streptavidin molecules.

Explosive sensor: peroxide explosives such as TATP can be detected using sensor devices with surface acidic group terminations, as acid peroxides tend to dissociate in presence of acidic groups; or using devices coated with metallic ionic substances such as $Zn^{2+}$, $In^{3+}$, $Sb^{3+}$, $Sc^{3+}$, $Ti^{4+}$ etc. Nitro based explosives can be detected using devices coated with a variety of dielectric materials that selectively react with activated nitro groups.

DNA sensor: an array of single stranded DNA oligomers, of any base pair lengths, can be attached to the surface of the devices, and used as layer 302. In this case, device 300 can be used to detect corresponding complementary DNA strands by way of DNA hybridization over the device surface. Device 300, coated with such an array of DNA strands, single stranded or double stranded depending on application, can be used for target DNA identification or for detection of specific ions or organic molecules, biomolecules, virus or bacteria, or the like. A large array of devices terminated with predetermined arrays of DNA oligomers can be used for DNA sequencing applications.

Nerve agent sensor: a Di-azo group, for example 3,5-dichlorophenyldiazomethane or its phenyl derivative, can be used as layer 302 to detect presence of Methylphosphonic Acid (MPA), which is a product of atmospheric hydrolysis of all nerve agents, and hence can detect presence of nerve agents in the ambient in a selective fashion. Or, layer 302 may include positive ion terminations of Cu++ on organic molecules, and sensor 300 can be used for high sensitivity measurement of nerve agents.

Metallo Porphyrin array sensor: a predetermined, select array of specific organic molecule monolayers and multilayers, for example Metallo porphyrins, can also be used as layer 302 to detect a variety of organic vapors in gas or ions in solutions with varying sensitivity and selectivity.

Mustard gas sensor: Layer 302 may include Guanine terminated DNA oligomer to sense sulfur mustard gas. Alternatively, layer 302 may include $Y_2O_3$ nano-crystals, to detect mustard gas.

Molecular Imprinted surface: Layer 302 may include "molecular imprinted" molecules or monolayers or multi layers or thin films or polymer matrices, that bind to a specific predetermined target molecule to realize highly selective sensors. By using an Epitome (a specific portion of a large molecule like protein) based approach, wherein the molecular imprint of the smaller Epitome in a monomer—cross linker matrix is used, larger molecules like proteins, DNA and other biomolecules are detected by selected binding at the Epitome site.

Ion sensor: Layer 302 may include specific organic molecules or inorganic thin films that can be used to sense ions in solution with high selectivity and sensitivity. For example, a thin film (e.g., a multilayer consisting of up to about three monolayers) of urea (N,N"-(9,10-dihydro-9,10-dioxo-1,2-anthracenediyl)bis[N'-phenyl] can be used to detect fluoride ion with high selectivity.

Figure 5:
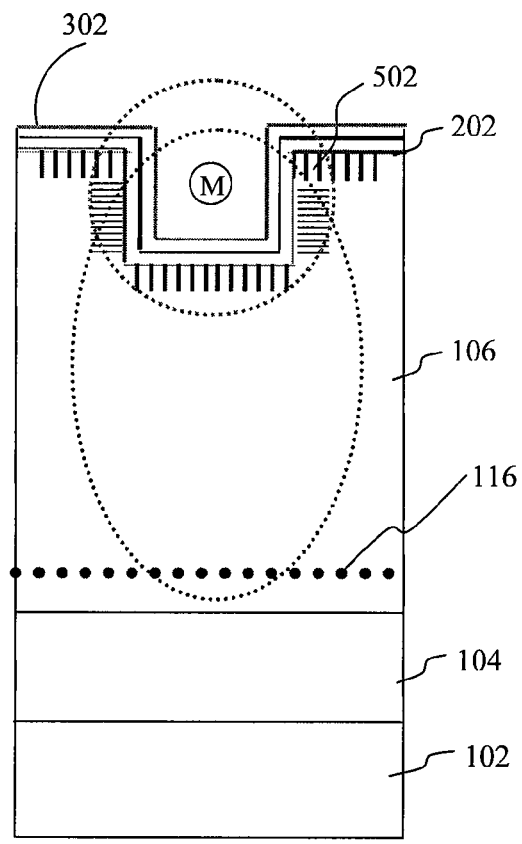
FIGS. 5-6 illustrate operation of the sensor illustrated in FIG. 3.

Forming pore and/or structures within region 106 not only increases the surface area of the active region of the sensor, but also increases a ratio of the interface state density at channel region 106—dielectric layer 202 interface to "the surface group density or charge density on surface 402. This concept is illustrated in FIG. 5. Upon binding of analyte molecule M at the surface of layer 302, a number of interface states 502 that come inside the potential field/electric field of influence of target species M is larger in the case where the surface is nano-structured, than the case where the surface is planar. This is done in order to optimize or maximize the modulation of occupancy and density of interface density states at channel region 106—dielectric layer 202 interface for a change in the charge at the sensitive layer 302 surface, or at the dielectric layer 202 surface.

Modulation of interface state occupancy at channel region 106-dielectric layer 202 interface, in-turn, changes the chemical potential of channel region 106 at the channel region 106-insulator 104 interface, in a fully depleted semi-conductor channel, causing a change in the threshold voltage of the inversion channel formed in channel 106 at the channel 106-insulator 104 interface. This indirect coupling of the field of species M causing modulation of occupancy of interface traps at channel 106-dielectric 202 interface, which in turn changes the threshold voltage of the inversion channel formed in channel 106, is termed as the fully depleted exponentially coupling (FDEC) effect, and any sensor with this as the working principle as an FDEC sensor.

In another case of the device structure, the same inversion channel conductance modulation can be achieved, rather than by modulation of interface state occupancy, by modulation of trapped charges or impurity doping and similar other charge center modulation in insulator 202 or in channel 106 due to binding of chemical moiety at the surface of the device.

Figure 6:
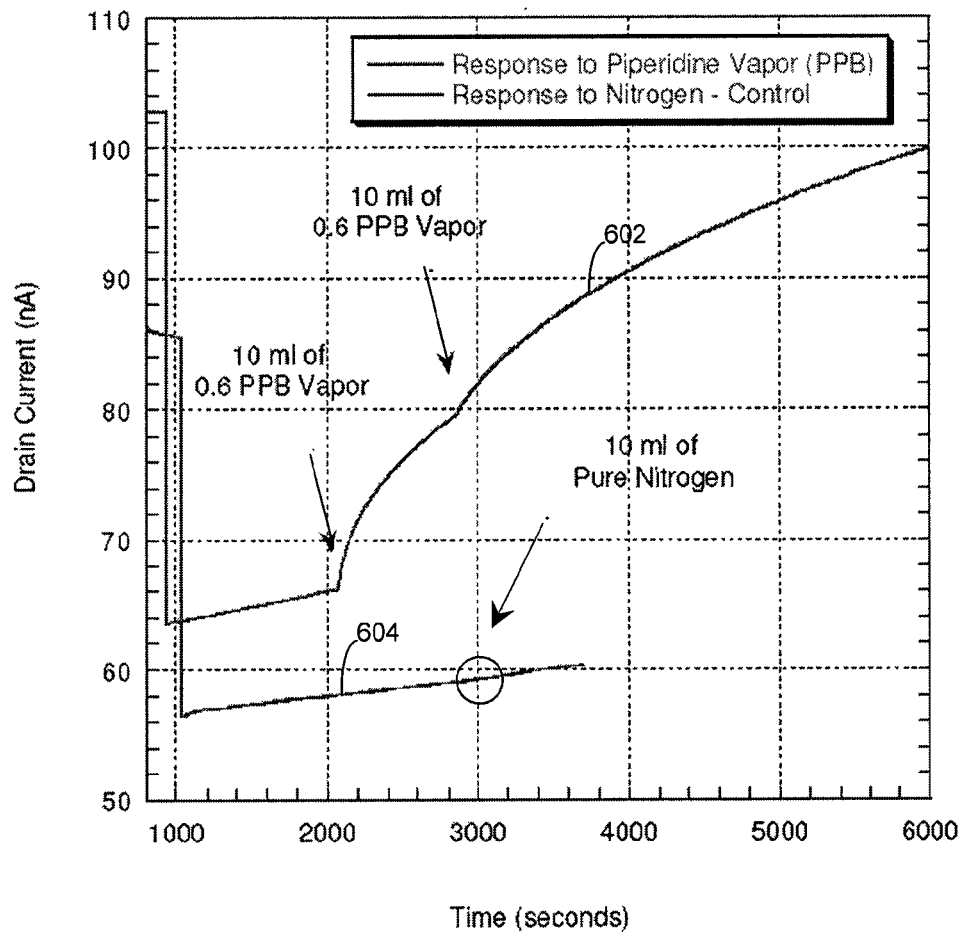

FIG. 6 illustrates a device response, where addition of electron donating species (piperidine molecules) to layer 302 (e.g., zinc porphyrin molecular monolayer), causes an increase in electron charge at the surface of dielectric layer 202 (e.g., a native silicon oxide) which in turn increases the electron inversion channel conductance (or drain current increases) in channel 106 (e.g., silicon) due to decrease in threshold voltage of the electron inversion channel 116. In the illustrated example, an increase in device drain current of a 500 nm device when the n-channel device is exposed to 0.6

PPB of piperidine molecules (line 602), compared to control experiment where just inert gas is introduced (line 604), establishes the device as a highly sensitive sensor.

Referring again to FIGS. 2-3, in accordance with various additional embodiments of the invention, one or more layers can be introduced between channel region 106 and dielectric layer 202. The nature of these layers can be insulating or semi insulating or semi conducting or semi metallic. One example of this is to use a thin layer of germanium, having a thickness of about 1 nm to about 100 nm sandwiched between channel region 106 and dielectric layer 202 or alternately, between channel region 106-dielectric layer 202 interface and insulator 104-channel region 106 interface. The stacking in this example could be Si (channel region 106), Ge (the extra layer) and oxide (dielectric layer 202) or Si (channel region 106), Ge (the extra layer), Si (another extra layer) and oxide (dielectric layer 202). In the same way, a stack of layers of different materials can be used between channel region 106 and dielectric layer 202. These extra layers may be desired to increase the efficiency of the sensor signal or for specific sensor applications. In all these examples of stacked structures, similar to the five-layer structure above (illustrated in FIG. 3), the addition of negative charge to the surface of an n-channel inversion based FET device (electrons are the carriers in inversion channel) increases the inversion channel conductance, and addition of positive charge to the surface decreases the inversion channel conductance; while addition of negative charge to the surface of a p-channel inversion based device (holes are the carriers in inversion channel) decreases the inversion channel conductance and addition of positive charge to the surface increases the inversion channel conductance.

Fabrication of specific examples:

Fabrication of a device in accordance with one embodiment of the invention is illustrated in FIGS. 7-14. The illustrated process can be used to form device 300, illustrated in FIG. 3 using silicon-on-insulator (SOI) inversion mode FET device, where base 102 is substrate silicon of an SOI wafer, insulator 104 is a buried oxide layer of the SOI wafer, channel region 106 is a porous or structured silicon on insulator layer, dielectric layer 202 is native oxide layer, and sensitive layer 302 is a chemical sensitive layer that binds specific target molecules in ambient, here a zinc porphyrin molecular monolayer. The exemplary process flow is for an n-channel, p-type bulk, silicon on insulator wafer using standard n-MOS process technology. It will be appreciated that fabrication can be done in a variety of ways, depending on the materials chosen for the various device layers, the process technology steps chosen to realize the sensor device, and the like.

Figure 7:
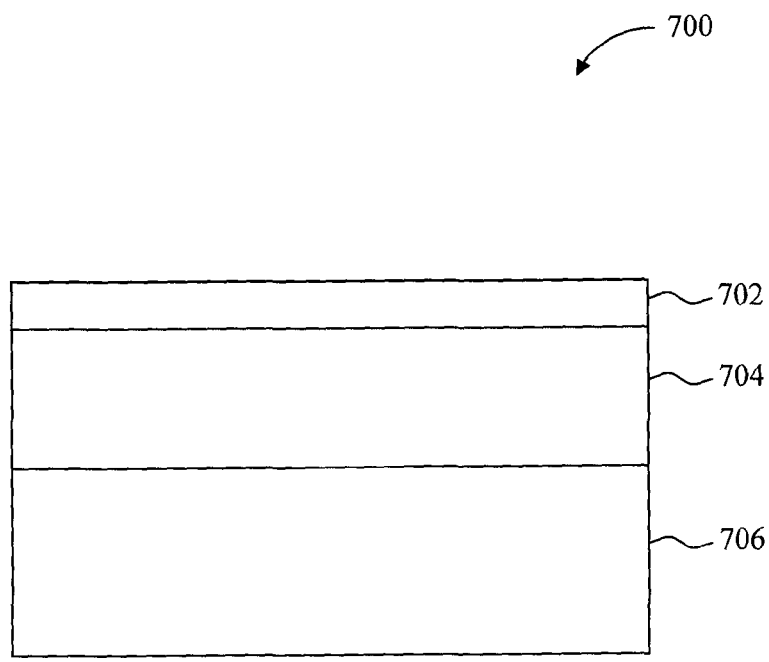
FIGS. 7-15 illustrate a method of forming a sensor in accordance with various embodiments of the invention.
Figure 8:
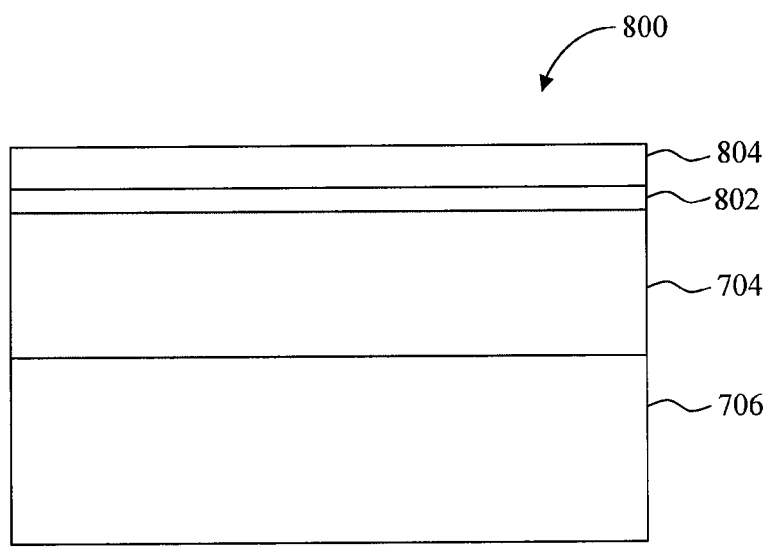
Figure 9:
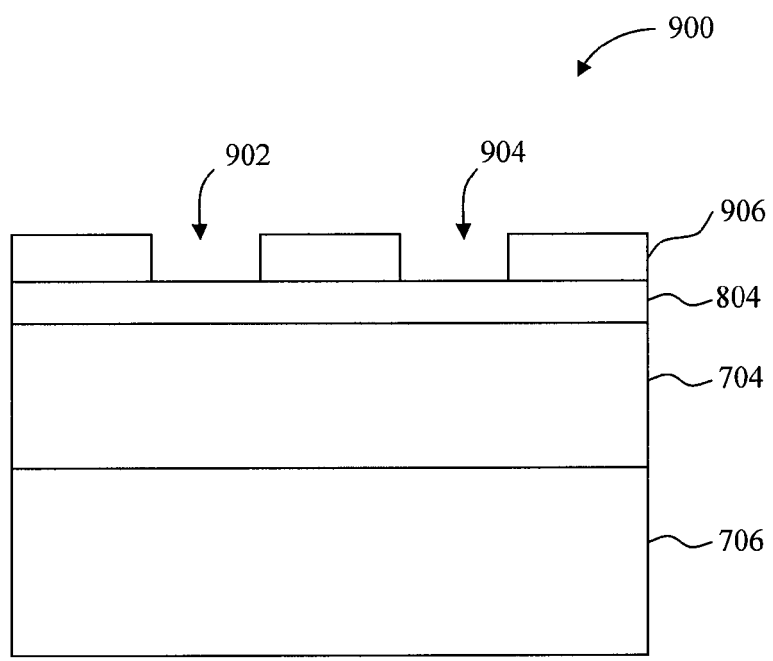
Figure 10:
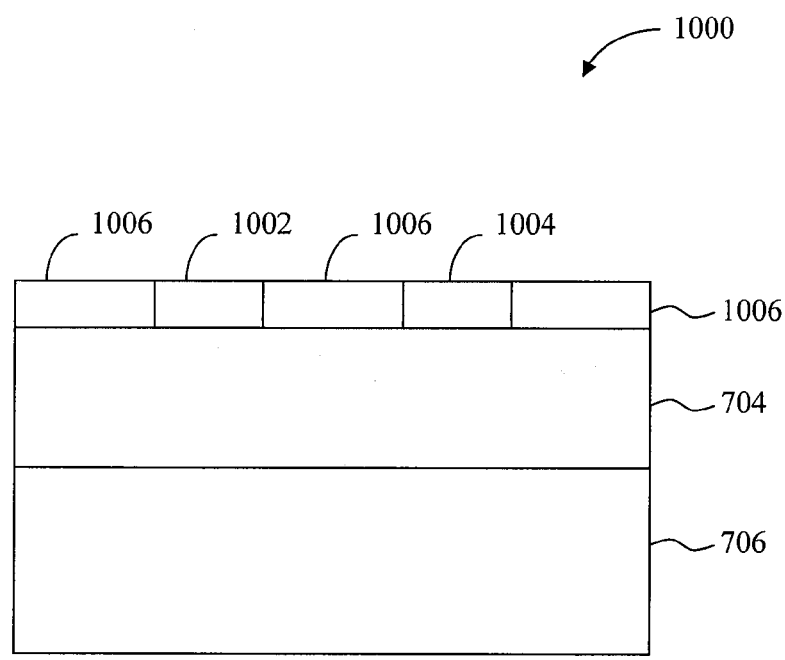

FIG. 7 illustrates a suitable starting material structure 700 for device 300 fabrication. Structure 700 is a p-type boron doped ($10^{15}$ cm$^3$) SOI wafer of resistivity ~20 Ohm-cm, produced using the separation by implanted oxygen SIMOX) process. An exemplary wafer can be obtained from IBIS technology Corporation. The initial thickness of a top silicon film layer 702 is greater than about 100 nm, with an underlying ion implanted buried oxide (BOX) layer 704 of thickness about 400 nm. Top silicon film 702 is thinned to about 100 nm using wet oxidation at about 1050° C. in a diffusion furnace for about 45 minutes, so that it is less than the Debye length of the minority carrier electrons (layer 802, illustrated in FIG. 8). Plasma enhanced chemical vapor deposition (PECVD) is performed to further increase the oxide thickness (layer 804). As discussed below, oxide layer 804 is also used as an effective mask for N+ phosphorous doping in subsequent processing. Next, positive photo resist OCG 825 is spin coated at about 4000 rpm for about 30 seconds to produce a photo resist layer, having a thickness of about 1000 Å. The resist is soft baked for about 15 minutes at about 80° C. A UV mask aligner is used to expose the resist for about 20 seconds through the n-well mask designed to open source drain windows for phosphorous doping. The exposed wafer is developed in OCG 945 developer for about 30 seconds, followed by a DI water rinse. The resist is then hard baked at about 115° C. for about 15 minutes. The hard baked resist protects the substrate during the buffered oxide etch (BOE) solution, which may be as long as about 30 minutes. Buffered oxide etch (BOE) is used to etch the top oxide for about 10 minutes to open the source drain doping windows 902, 904 in remaining oxide 906, as illustrated in FIG. 9. The photo resist is then stripped off using Microstrip 2000 stripper solution for about 20 minutes at about 100° C. Phosphorous doping of the exposed well regions on silicon is carried out in a solid source diffusion furnace at about 950° C. for about 30 minutes. Diffusion at about 950° C. for about 30 minutes gives an N+ junction depth on the order of one micron, with phosphorous doping density of $10^{19}$ cm$^{-3}$ and a resistivity of about 0.01 Ohm cm. Next, the masking oxide is removed by dipping the wafer in BOE for about 15 minutes, resulting in structure 1000, illustrated in FIG. 10, having doped regions 1002, 1004, and silicon region 1006.

Device isolation, in this process flow, is attained by physical separation of devices by plasma etching. On the other hand LOCOS or other suitable processes could alternatively be used for the device isolation.

Figure 11:
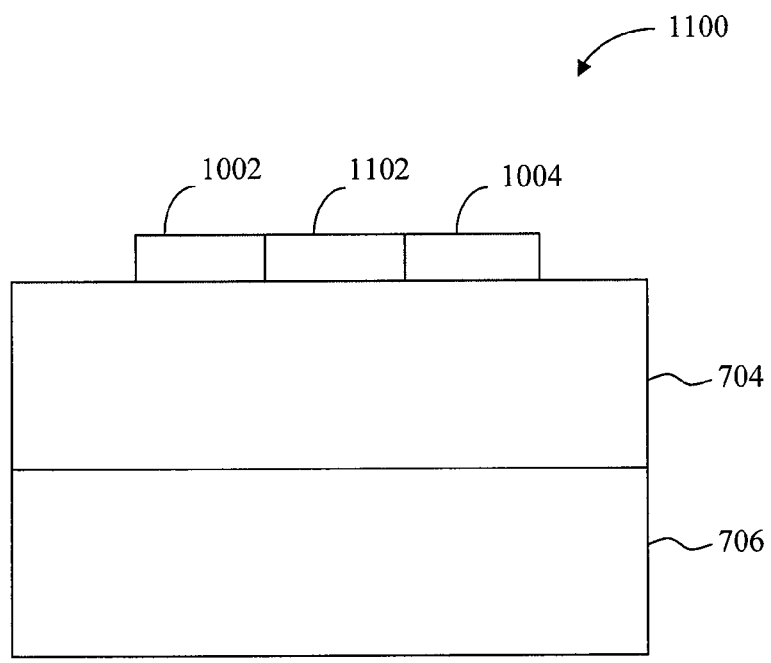

Turning now to FIG. 11, selective etching of silicon is carried out in a reactive ion etching (RIE) system using $SF_6$ etch chemistry. The wafer or substrate is spin coated with OCG825 photo resist and soft baked. The wafer is patterned with the active mask using the alignment marks as a guide, followed by photo resist development in OCG945 developer. The patterned photo resist is not hard baked for plasma etching of silicon. Silicon is selectively etched using $SF_6$ based gas chemistries-4 sccm of $SF_6$ gas flow at 20-millibar pressure, with 50 watt RF power applied for about 1 minute. The etch rate of silicon under these conditions is approximately 2000 Å per minute. The photo resist is then stripped off using Micro strip 2000 stripper solution. This results in structure 1100, which includes isolated silicon mesas 1102 on buried oxide 704, with source and drain regions 1002, 1004 on either side.

Figure 12:
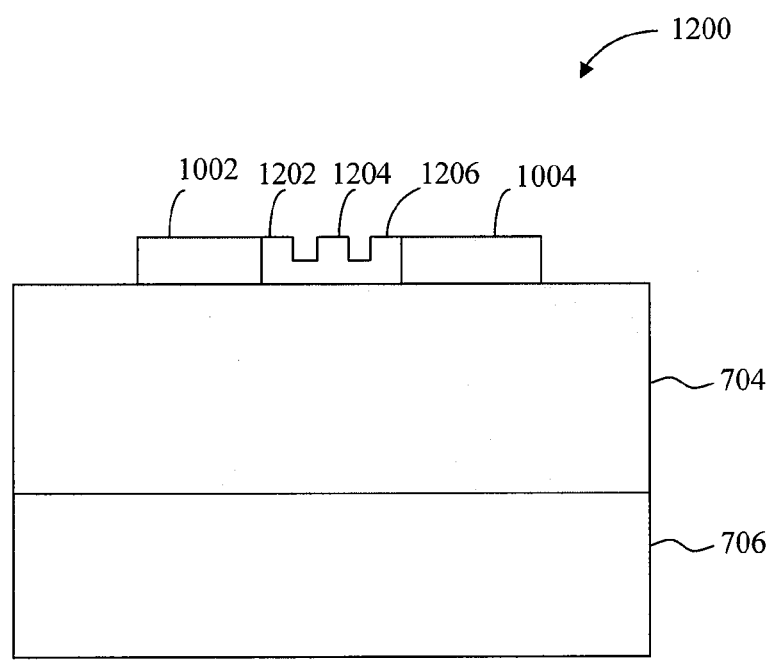
Figure 13:
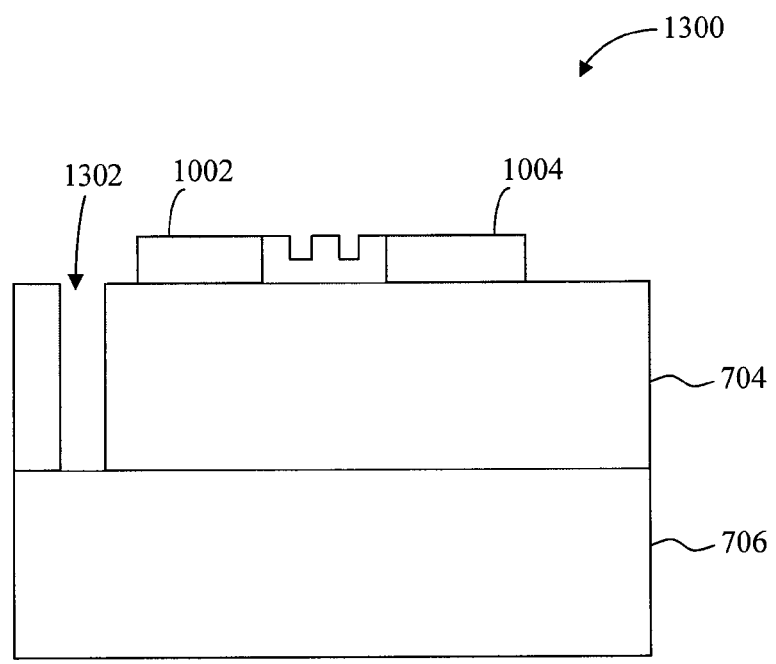
Figure 14:
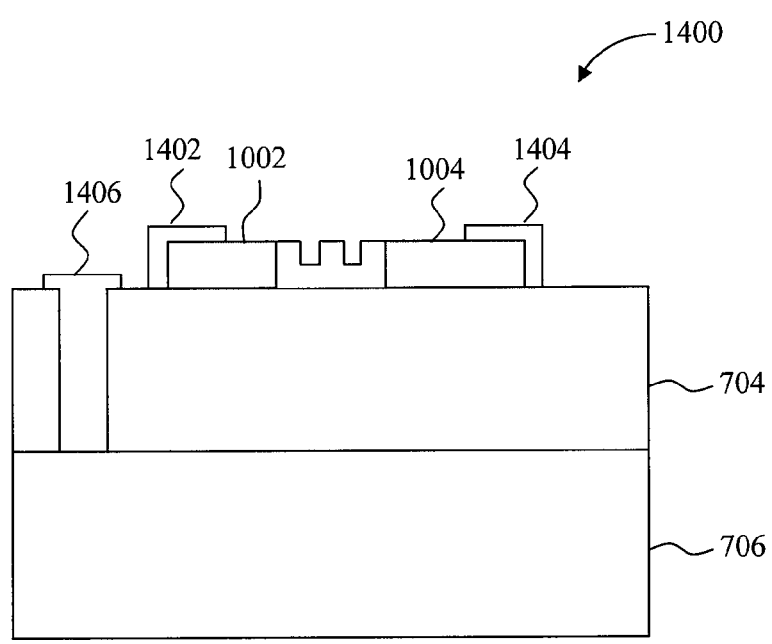

Silicon mesa 1102 surface is then coated with PMMA e-beam resist and patterned with e-beam lithography to obtain structure 1200, including structures 1202-1206 on the active area of the device surface, as illustrated in FIG. 12. The source-drain regions may be excluded by patterning accordingly, as it is not required as long as an ohmic contact is formed with the source and drain. Source drain regions can alternatively be masked by metal contacts, depending on process steps chosen. The design of the exposed pattern is such that continuous features with dimensions as small as 10 nm (could be as large as 100 nm or more) are obtained in, e.g., crisscross, straight line, pillar pattern, or any other desired pattern. RIE etch of patterned silicon structures is then performed to obtain a depth of few tens of nanometers (may be up to few hundreds of nanometers), to realize a three-dimensional, structured (e.g., nanostructured) pattern of any desired design. This surface may be further processed, depending on the application requirements, to obtain super-imposed pores (e.g., nanopores) of diameters ranging from tens of nanometers to less than few nanometers, and depths up to few tens or hundreds of nanometers. The same is also achieved by super-imposing micro and meso-pores structure on a macro porous structure.

In accordance with various embodiments of the invention, a surface of the active region 106 (excluding the source-drain regions) of the device 300 is made porous or structured, while maintaining the crystalline nature of the silicon all through the silicon channel even after processing. This acts to increase the interface trap density per target molecule binding, hence modulating the charge at the top interface and hence results in greater modulation of the inversion threshold voltage. A large variety of oxidant-based wet etching conditions can be used, such as techniques using HF solutions in aqueous and organic solvents, some in conjunction with illumination techniques. Porosity, pore dimensions, method of fabrication, method of electrical contact formation for anodization, etc. are determined by the specific application of the sensor. Anodization of top silicon active region (after formation of electrical contact) in 50% solution of HF in ethanol, at few tens of mill amp per square centimeter, for a period of few minutes to few tens of minutes, produces a meso porous structure on boron doped silicon. Similarly, by varying the conditions of etching, etc., micro porous, nano porous and macro porous silicon device surface can be attained, as per the application of the sensor. Other known techniques for realizing pore and/or structures such as template based selective etching or electrochemical etching or CVD deposition of silicon or molten state imprinting or laser etching or ion etching or particle etching or e-beam etching or chemically enhanced laser ablation can be alternatively used.

In accordance with one embodiment of the invention, silicon channel 1102 is not etched all the way down to the buried oxide. This is done in order to provide better electrical and mechanical properties at the porous/structured channel-buried oxide interface; and in order to get better turn on characteristics of the field effect sensor. Since the buried oxide, in this example, is formed by ion implantation, the silicon-buried oxide junction may not be mechanically strong. Over-etching of silicon channel may lead to undercutting of nanowires. Accordingly, a very thin layer of silicon (e.g., about 25 to about 30 nm) may desirably be left overlying the insulator.

Contact to substrate 706 be formed using a well etch through buried oxide layer 704, to allow for electrical contact with substrate 706. This substrate contact enables ease in bonding and probing. To form the contact, the wafer is spin coated with OCG825 resist and patterned with optical aligner to open contact holes. The resist is developed and hard baked for about 15 minutes at about 115° C. The etch rate of buried oxide in BOE is approximately 600 Å per minute. The 4000 Å buried oxide is etched in BOE for 15 minutes, allowing for a slight over etch. The over etch is performed since the Si/SiO$_2$ interface is gradual and not sharp; in order to make a good electrical contact with the substrate, the structure is further etched in RIE using CF4 plasma for 1 minute. CF$_4$ etches both Si and SiO$_2$, hence enabling a good contact of metal with the silicon substrate. The ME process recipe used is 50 sccm of CF4 at 50 millibar pressure with an applied RF power of 50 Watts. The photo resist is then stripped off in Microstrip 2000 solution, resulting in structure 1300, including a trench 1302.

To form the metal contacts, the wafer is spin coated with OCG825 resist and soft baked at 80° C. The wafer is patterned with a metal mask using optical aligner and developed. 2500 Å of gold is deposited on the exposed windows to make ohmic contacts 1402, 1404, with the source drain regions and contact 1406 to substrate 706. To get thicker gold metal layers AZ4330 resist is used. After deposition of gold, using either e-beam or thermal evaporation tools, lift off is carried out in acetone at 50° C. for half an hour. The device surface is then treated in Buffered Oxide Etch (BOE) for 15 seconds, and fresh oxide of thickness 2 nm is grown on the silicon surface by immersing in hydrogen peroxide solution for thirty minutes. This can also be achieved by deposition of PECVD oxide or growth of wet oxide in particular conditions.

Figure 15:
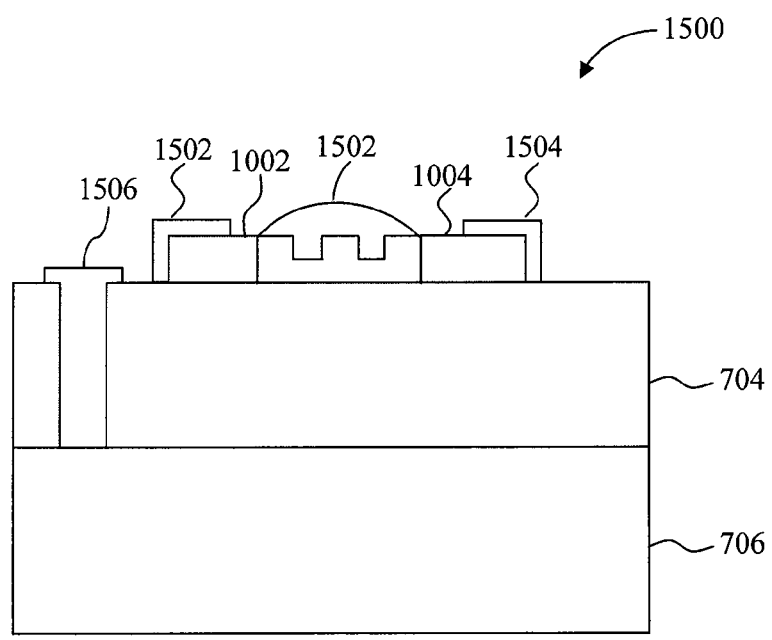

Finally the surface of the device is coated with the chemical sensitive layer (e.g., layer 1502, illustrated in FIG. 15), which is predetermined to sense a specific target molecule. The surface coating of the chemical sensitive layer can be achieved by any of the process technologies. An example of this is coating of the device surface with metalloporphyrin monolayer (Langmuir Blodgett or by covalent attachment or contact imprint or similar technologies), which is sensitive to binding of amine molecules at the positively charged center metal atom.

Although the present invention is set forth herein in the context of the appended drawing figures, it should be appreciated that the invention is not limited to the specific form shown. For example, while the sensor device structures are conveniently described above in connection with a silicon substrate, the invention is not so limited; the structure of the present invention may additionally or alternatively be formed on alternative substrates. Furthermore, although only some of the devices are illustrated with particular layers, the devices and structures of the present invention may include additional layers, which are not illustrated. Various other modifications, variations, and enhancements in the design and arrangement of the method and apparatus set forth herein, may be made without departing from the spirit and scope of the present invention as set forth in the appended claims.

I claim:

1. A sensor for detecting a biological, chemical, or radioactive species, the sensor comprising:
   a substrate;
   an insulator formed overlying a portion of the substrate; and
   a channel formed overlying the insulator, wherein the channel surface comprises structures or pores formed therein, and
   wherein the sensor is configured to operate in a fully depleted mode, such that a sensed biological, chemical, or radioactive species causes an exponential change in channel conductance of the field effect sensor,
   wherein the channel comprises a plurality of structures and wherein a width of each of the plurality of structures is from about 10 Angstrom to 10 millimeters, and
   wherein the plurality of structures have different widths.

2. The sensor for detecting a biological, chemical, or radioactive species of claim 1, wherein the substrate, the insulator and the channel are formed from a silicon-on-insulator substrate.

3. The sensor for detecting a biological, chemical, or radioactive species of claim 1, wherein a width of the channel ranges from about 10 Angstrom to about 10 millimeters.

4. The sensor for detecting a biological, chemical, or radioactive species of claim 1, further comprising a dielectric material layer overlying the channel, wherein the dielectric layer is either a continuous layer or discrete islands.

5. The sensor for detecting a biological, chemical, or radioactive species of claim 4, wherein the dielectric material comprises material selected from the group consisting of SiO$_2$, Si$_3$N$_4$, SiNx, Al2O$_3$, AlOx La2O$_3$, Y2O$_3$, ZrO$_2$, Ta$_2$O$_5$, HfO$_2$, HfSiO$_4$, HfOx, TiO$_2$, TiOx, a-LaAlO$_3$, SrTiO$_3$, Ta$_2$O$_5$, ZrSiO$_4$, BaO, CaO, MgO, SrO, BaTiO$_3$, Sc$_2$O$_3$, Pr$_2$O$_3$, Gd$_2$O$_3$, Lu$_2$O$_3$, TiN, CeO$_2$, BZT, BST, PVP—poly(4-vinyl phenol), PS—polystyrene, PMMA—polymethyl-methacrylate, PVA—polyvinyl alcohol, PVC—polyvinylchloride, PVDF—polyvinylidenfluoride, PaMS—poly[α-methylstyrene], CYEPL—cyano-ethylpullulan, BCB—divinyltetramethyldisiloxane-bis(benzocyclobutene), CPVP-Cn, CPS-Cn, PVP-CL, PVP-CP, polynorb, GR, nano $TiO_2$, OTS, Pho-OTS, and combinations thereof.

6. The sensor for detecting a biological, chemical, or radioactive species of claim 5, wherein the dielectric material comprises $SiO_2$.

7. The sensor for detecting a biological, chemical, or radioactive species of claim 1, further comprising a layer comprising a material selected from the group consisting of an antibody sensor, explosive material sensor, protein sensor, bio-molecule sensor, a DNA sensor, a DNA hybridization sensor, a toxic gas sensor, nerve agent sensor, a mustard gas sensor, a sensor consisting of a molecular imprinted surface, and an ion sensor.

8. A method of forming a solid-state sensor, the method comprising the steps of:
providing a substrate;
forming an insulator overlying the substrate;
forming a porous channel region overlying the insulator;
forming a chemical, biological, or radioactive sensitive material overlying the porous channel region, and
forming a dielectric layer overlaying the porous channel region.

9. The method of claim 8, wherein the chemical, biological, or radioactive sensitive material is formed overlying the dielectric layer.

10. The sensor for detecting a biological, chemical, or radioactive species, the sensor comprising:
a substrate;
an insulator formed overlying a portion of the substrate; and
a channel formed overlying the insulator, wherein the channel surface comprises structures or pores formed therein; and
a dielectric material layer overlying the channel, wherein the dielectric layer is either a continuous layer or discrete islands,
wherein the sensor is configured to operate in a fully depleted mode, such that a sensed biological, chemical, or radioactive species causes an exponential change in channel conductance of the field effect sensor,
wherein the channel comprises a plurality of structures and wherein a width of each of the plurality of structures is from about 10 Angstrom to 10 millimeters, and
wherein the channel is fully depleted without any need for gate bias.

11. The sensor for detecting a biological, chemical, or radioactive species of claim 10, wherein the dielectric layer comprises organic dielectric material or inorganic dielectric material.

12. The sensor for detecting a biological, chemical, or radioactive species of claim 10, wherein the dielectric material comprises organic dielectric material.

13. The sensor for detecting a biological, chemical, or radioactive species of claim 10, wherein the dielectric material comprises inorganic dielectric material.

14. The sensor for detecting a biological, chemical, or radioactive species of claim 10, wherein the plurality of structures have different widths.

15. The sensor for detecting a biological, chemical, or radioactive species of claim 10, further comprising a layer comprising a material selected from the group consisting of an antibody sensor, explosive material sensor, protein sensor, bio-molecule sensor, a DNA sensor, a DNA hybridization sensor, a toxic gas sensor, nerve agent sensor, a mustard gas sensor, a sensor consisting of a molecular imprinted surface, and an ion sensor.

16. The sensor for detecting a biological, chemical, or radioactive species, the sensor comprising:
a substrate;
an insulator formed overlying a portion of the substrate; and
a channel formed overlying the insulator, wherein the channel surface comprises structures or pores formed therein; and
wherein the sensor is configured to operate in a fully depleted mode, such that a sensed biological, chemical, or radioactive species causes an exponential change in channel conductance of the field effect sensor,
wherein the channel comprises a plurality of structures and wherein a width of each of the plurality of structures is from about 10 Angstrom to 10 millimeters, where the substrate is made of flexible material.

17. A sensor for detecting a biological, chemical, or radioactive species, the sensor comprising:
a substrate;
an insulator formed overlying a portion of the substrate; and
a channel formed overlying the insulator, wherein the channel surface comprises structures or pores formed therein; and
wherein the sensor is configured to operate in a fully depleted mode, such that a sensed biological, chemical, or radioactive species causes an exponential change in channel conductance of the field effect sensor,
wherein the channel comprises a plurality of structures and wherein a width of each of the plurality of structures is from about 10 Angstrom to 10 millimeters, and
wherein the channel is an n-channel structure and addition of negative charge to a surface of the channel causes an exponential increase of inversion channel conductance, the channel is an n-channel structure and addition of a positive charge to the surface of the channel causes an exponential decrease of the inversion channel conductance the channel is a p-channel structure and addition of a negative charge to a surface of the channel causes an exponential decrease of the inversion channel conductance, or the channel is a p-channel structure and addition of a positive charge to the surface of the channel causes an exponential increase of the inversion channel conductance.

18. The sensor for detecting a biological, chemical, or radioactive species of claim 17, wherein the substrate, the insulator, and the channel are formed from a silicon-on-insulator substrate.

19. The sensor for detecting a biological, chemical, or radioactive species of claim 17, wherein a width of the channel ranges from 10 Angstrom to about 10 millimeters.

20. The sensor for detecting a biological, chemical, or radioactive species of claim 17, further comprising a dielectric material layer overlying the channel, wherein the dielectric layer is either a continuous layer or discrete islands.

21. The sensor for detecting a biological, chemical, or radioactive species of claim 20, wherein the dielectric material comprises material selected from the group consisting of $SiO_2$, $Si_3N_4$, $SiN_x$, $Al_2O_3$, $AlO_x$ $La_2O3$, $Y_2O_3$, $ZrO_2$, $Ta_2O_5$, $HfO_2$, $HfSiO_4$, $HfO_x$, $TiO_2$, $TiO_x$, a-$LaAlO_3$, $SrTiO_3$, $Ta2O_5$, $ZrSiO_4$, BaO, CaO, MgO, SrO, $BaTiO_3$, $Sc_2O_3$, $Pr_2O_3$, $Gd_2O_3$, $Lu_2O_3$, TiN, $CeO_2$, BZT, BST, PVP—poly(4-vinyl phenol), PS—polystyrene, PMMA—polymethyl-methacrylate, PVA—polyvinyl alcohol, PVC—polyvinylchloride, PVDF—polyvinylidenfluoride, PαMS—poly[α-methylstyrene], CYEPL—cyano-ethylpullulan, BCB—divinyltetramethyldisiloxane-bis(benzocyclobutene), CPVP-Cn, CPS-Cn, PVP-CL, PVP-CP, polynorb, GR, nano $TiO_2$, OTS, Pho-OTS, and combinations thereof.

22. The sensor for detecting a biological, chemical, or radioactive species of claim 20, wherein the dielectric material comprises $SiO_2$.

23. The sensor for detecting a biological, chemical, or radioactive species of claim 20, wherein the dielectric material comprises organic dielectric material.

24. The sensor for detecting a biological, chemical, or radioactive species of claim 20, wherein the dielectric material comprises inorganic dielectric material.

25. The sensor for detecting a biological, chemical, or radioactive species of claim 17, wherein the plurality of structures have different widths.

\* \* \* \* \*